United States Patent [19]
Reis

[11] Patent Number: 5,961,474
[45] Date of Patent: Oct. 5, 1999

[54] NON-INVASIVE MEASUREMENT OF JOINT TRANSLATION AND RANGE OF MOTION

[76] Inventor: Mark T. Reis, 24285 Johnson Rd., Poulsbo, Wash. 98370

[21] Appl. No.: 09/045,323

[22] Filed: Mar. 20, 1998

[51] Int. Cl.$^6$ ..................................................... A61B 5/00
[52] U.S. Cl. ......................................................... 600/595
[58] Field of Search ................................... 600/587, 592, 600/594, 595

[56] References Cited

U.S. PATENT DOCUMENTS

| | | | |
|---|---|---|---|
| 4,849,692 | 7/1989 | Blood | 324/208 |
| 4,945,305 | 7/1990 | Blood | 324/207.17 |
| 5,588,444 | 12/1996 | Petragallo | 600/595 |
| 5,600,330 | 2/1997 | Blood | 324/463 |

OTHER PUBLICATIONS

"Accuracy of an Electromagnetic Tracking Device: A study of the Optimal Operating Range and Metal Interference", Milne et al., J. Biomechanics, vol. 29, No. 6, pp. 791–793, 1996.

"A New Dynamic Testing Apparatus to Study Glenohumeral Joint Motion", R. Debski et al., J. Biomechanics, vol. 28, No. 7, pp. 869–874, 1995.

"Shoulder instability" "Assessment of anterior–posterior translation with a knee laxity tester", Jorgensen et al., Acta Orthop Scand 1995; 66 (5) : 398–400.

"Laxity of the normal glenohumeral joint: A quantitative in vivo assessment", D. Harryman II et al., J. Shoulder Elbow Surg., Mar./Apr. 1992, vol. 1., No. 2, pp. 66–76.

"Translation of the glenohumeral joint with the patient under anesthesia", R. Hawkins et al., J. Shoulder Elbow Surg., Jul./Aug. 1996, vol. 5, No. 4, pp. 286–292.

"Intra–and Interobserver Reproducibility of the Shoulder Laxity Examination", A. Levy et al., Shoulder: Instability, Paper No. 285, Moscone Center Room 135, Feb. 14, 1997.

"Genucom, KT–1000, and Stryker knee laxity measuring device comparisons" "Device reproducibility and interdevice comparison in asymptomatic subjects", C. Highenboten et al., The American Journal of Sports Medicine, vol. 17, No. 6, 1989, pp. 743–746.

"Role of KT–1000 Exam and Instrumented Testing", R. Mangine, Advances on the Knee and Shoulder, May 24, 1992.

"Translation of the Humeral Head on the Glenoid with Passive Glenohumeral Motion", D. Harryman, et al., The Journal of Bone and Joint Surgery, Inc., Oct. 1990, vol. 72-A, No. 9, pp. 1334–1343.

(List continued on next page.)

*Primary Examiner*—Max Hindenburg
*Attorney, Agent, or Firm*—Andrus, Sceales, Starke & Sawall

[57] ABSTRACT

Electromagnetic position sensors are placed on the skin of a patient to electronically measure joint translation and range of motion. Non-invasive monitoring is provided during a joint translation examination by placing one position sensor on the skin of the patient to measure the position of a first bone in the vicinity of the joint and another position sensor on the skin of the patient to measure the position of a second bone in the vicinity of the joint. The translation examination is then conducted by the attending physician, and the amount of joint translation is determined objectively by determining the difference in the relative position between the sensors from an initial position for the exam to a clinical end point for the exam. In a glenohumeral translation examination, one sensor is preferably placed on the skin over the scapular spine while the other sensor is preferably placed over the bicipital groove. In a shoulder range of motion examination, the sensor over the bicipital groove is moved to cover the biceps. Again, the range of motion is determined objectively by determining the difference in the relative position between the sensors from an initial position for the exam to a clinical end point for the exam. The invention can be used to objectively monitor translation and range of motion of other joints as well.

29 Claims, 7 Drawing Sheets

OTHER PUBLICATIONS

"Instrumented Measurement of Anterior Laxity of the Knee", D. Daniel et al., The Journal of Bone and Joint Surgery, Inc., vol. 67–A, No. 5, Jun., 1985, pp. 720–725.

"Arthrometric Evaluation of Knees That Have a Torn Anterior Cruciate Ligament", B. Bach et al., The Journal of Bone and Joint Surgery, Inc., vol. 72–A, No. 9, Oct. 1990, pp. 1299–1306.

"The Role of the Rotator Interval Capsule in Passive Motion and Stability of the Shoulder", D. Harryman, II et al., The Journal of Bone and Joint Surgery, Inc., vol. 74–A, No. 1, Jan. 1992, pp. 53–66.

"Multidirectional instability: Current concepts", W. Mallon et al., J. Shoulder Elbow Surg., Jan./Feb. 1995, pp. 54–64.

"Posterior Shoulder Laxity in Asymptomatic Athletes", E. McFarland et al., The American Journal of Sports Medicine, vol. 24, No. 4, 1996, pp. 468–471.

"The Flock of Birds™ Installation and Operation Guide", Ascention Technology Corporation, POB 527, 1995, pp. 1–123.

Ascension Technology Corporation Sales Literature dated Aug. 12, 1996 or earlier.

NON-INVASIVE MEASUREMENT OF JOINT TRANSLATION AND RANGE OF MOTION

FIELD OF THE INVENTION

The invention relates to the measurement of joint laxity and range of motion for orthopedic patients in clinical settings. In particular, the invention involves the use of non-invasive position sensors placed on the skin of a patient to facilitate objective measurement of joint translation and range of motion.

BACKGROUND OF THE INVENTION

In clinical settings, the evaluation of joint stability and range of motion is for the most part based on the subjective analysis of the examining physician. Orthopedic physicians normally evaluate joint stability by conducting an examination to subjectively observe joint translation (i.e. relative displacement of bones articulated at the joint due). The amount of joint translation is evaluated by pushing or pulling on one or more of the bones articulating at the joint in a specific direction to a clinical end point, and evaluating the relative displacement of the bones at the joint by subjective physical observation. Likewise, joint range of motion is normally evaluated by bending or rotating the joint to a clinical end point, and evaluating the range of motion of the joint by subjective physical observation. In general, there are two types of range of motion examinations: active and passive.

Due to the subjective nature of joint translation and range of motion examinations, reliable and precise assessment of joint laxity and range of motion can be difficult. There has been a need in the field to provide more objective assessment of joint laxity and range of motion for patients in a variety of clinical settings. Objective information may help relatively inexperienced physicians and other practitioners confirm a diagnosis of joint instability or loss of motion. Also, real time display of objective information may in fact facilitate proper examination techniques by inexperienced physicians. Further, objective information would allow for more accurate assessments of the results of surgery designed to restore joint stability and/or range of motion. Objective information on joint stability and/or range of motion would also be useful when seeking a second opinion of a physician not present at the physical exam, as well as documenting an initial diagnosis or chronologically documenting a recovery process.

Static or dynamic radiographic methods may be used to objectively assess and document joint translation and range of motion, however, radiographic methods are impractical, especially in office settings. In addition, it is not desirable to expose patients to unnecessary radiation.

SUMMARY OF THE INVENTION

The invention involves the use of at least two non-invasive position sensors placed on the skin of the patient to objectively measure joint translation and/or range of motion. Use of the invention provides accurate and reproducible objective data on joint translation and/or range of motion in a relatively simple and inexpensive manner.

To objectively measure joint translation, a first position sensor is placed on the skin of the patient in a location suitable for measuring the position of one of the bones in the vicinity of the joint. For instance, when measuring glenohumeral translation of the shoulder joint, the first position sensor is placed over the scapula, such as over the scapular spine or the acromion portion of the scapula, to indicate the relative position of the glenoid of the scapula. A second position sensor is placed on the skin of the patient in a location appropriate for measuring the position of a second bone articulated at the joint in the vicinity of the joint. In measuring a glenohumeral translation, the second sensor is placed on the skin at a location corresponding to the humeral head of the patient, such as over the bicipital groove at the anterior of the patient's shoulder. A conventional joint translation physical examination is then conducted by the examiner, and signals from the first and second position sensors are used to accurately and objectively display and document the amount of joint translation. Cutaneous mounting of the position sensors on the patient (i.e. mounting on the skin of the patient) allows the invention to be implemented easily in an office setting. Also, the patient is not subjected to radiation or painful pin insertion techniques that have been previously used in experiments.

With the position sensor properly placed on the skin of a patient, the physical translation examination is preferably accomplished in the following manner. The first and second bone articulated at the joint are positioned in a clinical neutral position (e.g. in a glenohumeral translation exam, the humeral head is centered within the glenoid), and initial position signals from the first and second position sensors are generated and stored in electronic memory. The examiner then applies force to move one bone articulated at the joint with respect to the other bone to a clinical end point. At the clinical end point, signals from the first and second position sensors are again generated and stored in electronic memory. The relative position of the first and second position sensors is determined both when the joint is in the clinical neutral position and when the joint is at the clinical end point. Objective measurement of joint translation is provided electronically by comparing the relative position between the first and second position sensors when the joint is in the clinical neutral position to the relative position between the first and second position sensors when the joint is at the clinical end point.

As described, the invention produces precise and highly reproducible joint translation data. For instance, testing with experienced orthopedic physicians conducting glenohumeral translation repeated examinations have shown nearly identical reproducibility. In addition, the direction of joint translation as determined from the difference of the relative position of the position sensors can be compared to a preselected clinical translation direction to facilitate consistent joint translation examination technique. This may be useful for relatively inexperienced examiners, or for subsequent examination by a different physician.

To objectively measure joint range of motion, it is preferred that the second position sensor be placed on the skin of the patient at a location away from the joint (e.g. in measuring shoulder range of motion, the second position sensor is preferably placed over the middle of the biceps of the patient) to measure the position of the second bone articulated at the joint. A conventional active or passive range of motion examination is then conducted by the attending orthopedic physician. Joint range of motion measured in angle degrees is otherwise measured in much the same manner as explained above with respect to joint translation to provide accurate, objective data regarding joint range of motion.

To implement the invention, it is preferred to use a system that employs electromagnetic position sensors such as the systems commercially available from Ascension Technology Corporation, Burlington, Vt., which are disclosed in U.S. Pat. Nos. 4,849,692; 4,945,305; and 5,600,330, and are incorporated herein by reference. In the preferred system, a programmed computer controls operation of the electromagnetic sensors and also includes software and screen displays to facilitate real time feedback to the attending orthopedic physician regarding the translation and/or range of motion examination. For instance, it is desirable that the computer include software that calculates joint translation and range of motion values and displays the values on a screen display. The software preferably provides a pictorial simulation of the joint on the screen display during translation and/or range of motion examinations. In addition, the electromagnetic position sensors are preferably part of sensor assemblies that are customized with features to facilitate efficient use during joint translation and/or range of motion examinations.

Other features and advantages of the invention may be apparent to those skilled in the art upon inspecting the following drawings and description thereof.

DETAILED DESCRIPTION OF THE DRAWINGS

Figure 1:
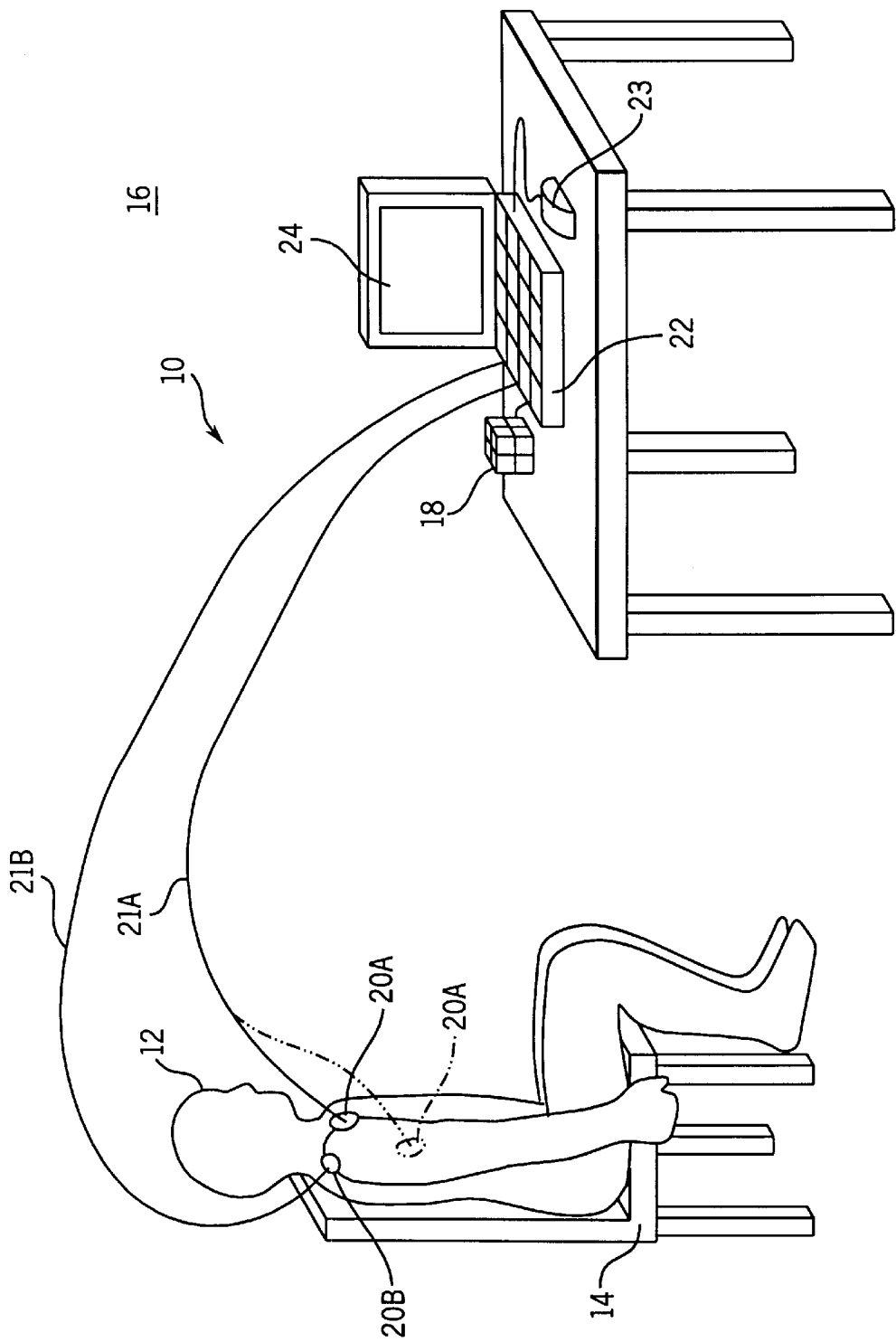
FIG. 1 is a schematic view illustrating the use of an electronically controlled electromagnetic position sensing system used to measure joint translation and range of motion of a patient's shoulder in accordance with the invention.

FIG. 1 is a schematic illustration of a system 10 that measures shoulder range of motion and/or glenohumeral translation of a patient 12 in accordance with the invention. The patient 12 is sitting on an examination chair 14 in an examination room 16. The system 10 includes an electromagnetic transmitter 18, a first electromagnetic position sensor 20A, a second electromagnetic position sensor 20B, and a programmed computer 22. The programmed computer 22 is a personal computer equipped with a mouse 23, a screen display 24 and electronic hardware to drive the transmitter 18 and process signals from electromagnetic position sensors 20A, 20B as disclosed in the above-incorporated U.S. Pat. Nos. 4,849,692; 4,945,305; and 5,600,330.

As discussed in the above-incorporated patents, the transmitter 18 provides a low-level pulsed direct current magnetic field in the examination room 16. The transmitter 18 preferably consists of three individual antennae arranged concentrically to generate a multiplicity of DC magnetic fields that are picked up by the electromagnetic position sensors 20A, 20B. The electromagnetic position sensors 20A, 20B measure not only the fields generated by the transmitter 18, but also the earth's magnetic field. For accuracy, it is important that the transmitter 18 be mounted on a non-ferromagnetic surface, such as a wooden table. In addition, the electromagnetic position sensors 20A, 20B should be located within a reasonable distance from the transmitter 18, e.g. within approximately 12 feet from the transmitter 18. The transmitter 18 antennae are orthogonal (i.e., an X-axis antenna, a Y-axis antenna and a Z-axis antenna). The electromagnetic position sensors 20A, 20B also preferably have three orthogonal antennae (i.e. an X, Y and Z-axis antenna). The electromagnetic position sensors 20A, 20B generate a position signal which is transmitted via line 21A, 21B, respectively, to signal processing electronics preferably located on an electronic card located within the programmed computer 22. The analog signals in lines 21A, 21B are filtered and converted into digital signals representing the position of the electromagnetic position sensors 20A, 20B in the electromagnetic field produced by the transmitter 18. The signal processing electronics at the computer 22 filter the signals in lines 21A, 21B for noise, and also account for the effect of the earth's electromagnetic field on the signals.

The system as described is capable of measuring the displacement and the orientation of the electromagnetic position sensors 20A, 20B in six degrees of freedom (e.g. displacement and rotation with respect to the X, Y and Z axes in the Cartesian coordinate system). However, the three rotational degrees of freedom, as well as one of the displacement degrees of freedom are not necessary for implementing the most fundamental forms of the invention. That is, clinical joint translation and range of motion examinations are easily repeatable with respect to the rotation of the joint and with respect to displacement in the direction of the Z-axis. Therefore, the invention generally requires measuring of displacement in the direction of X-axis and Y-axis only. The absolute accuracy of the electromagnetic position sensors 20A, 20B in the electromagnetic field is approximately 0.07 inches RMS, with a resolution of approximately 0.02 inches RMS.

In FIG. 1, the patient 12 is sitting in an upright position on the examination chair 14 with the electromagnetic position sensors 20A, 20B placed on the skin of the patient in the appropriate position for a glenohumeral translation examination. For a shoulder range of motion examination, the first electromagnetic position sensor 20A is moved over the patient's biceps as shown in phantom in FIG. 1.

Figure 9:
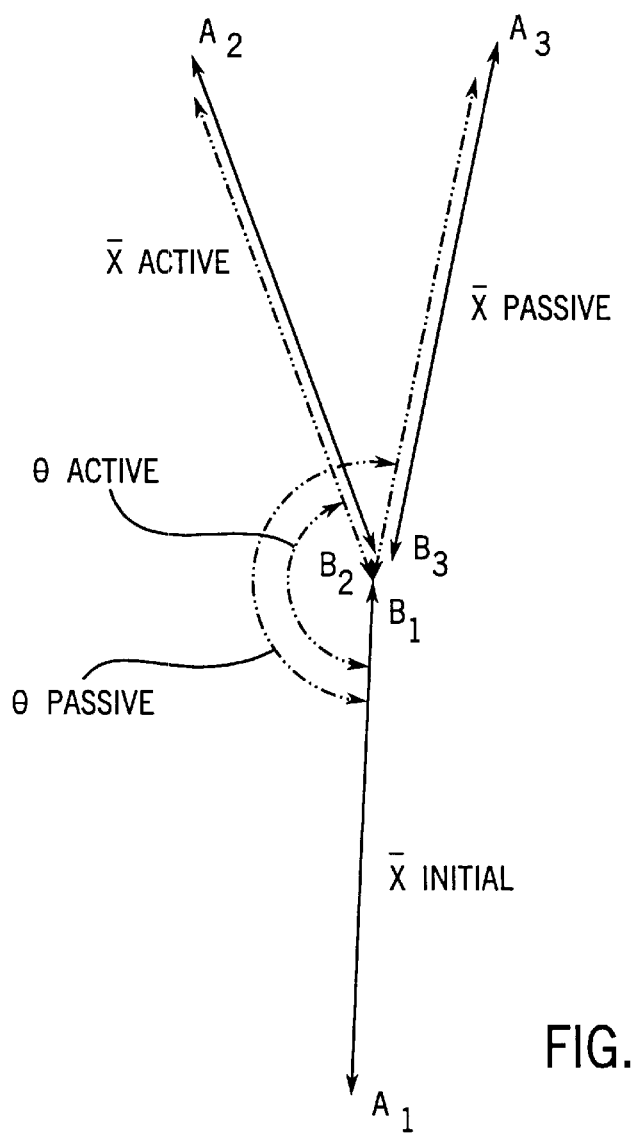
FIG. 9 is a vector diagram illustrating the measurement of joint range of motion in accordance with the invention.

FIGS. 2–7 relate to measuring the glenohumeral translation using the invention. FIGS. 8 and 9 relate to measuring shoulder range of motion using the invention. It should be noted, however, that the invention is not limited to monitoring joint translation and range of motion of the shoulder joint. The invention can be applied to other joints in the human body, such as the elbow, the knee, the ankle, the neck, etc. Application of the invention to other joints should be apparent to those skilled in the art upon gaining an understanding of how the invention operates to monitor glenohumeral translation and/or shoulder range of motion.

Referring now to FIGS. 2–7, FIG. 2 is a detailed view showing the second position sensor 20B placed on the skin of a patient to the posterior of the shoulder. The purpose of the second position sensor 20B is to monitor the position of the glenoid of the scapula. Preferably, the second position sensor 20B is attached on the skin of the patient over the scapular spine or over the acromion. Adhesive, such as tape, can be used to fix the position of the second position sensor 20B on the skin over the scapular spine or the acromion. It is important that the position of the sensor 20B does not move significantly with respect to the scapula during the monitoring process. FIG. 4A shows the preferred embodiment of sensor 20B in which a cutaneous gel-based mount 26, such as conventionally used on electrocardiogram sensors, is used on the bottom surface of the sensor 20B.

Figure 4A:
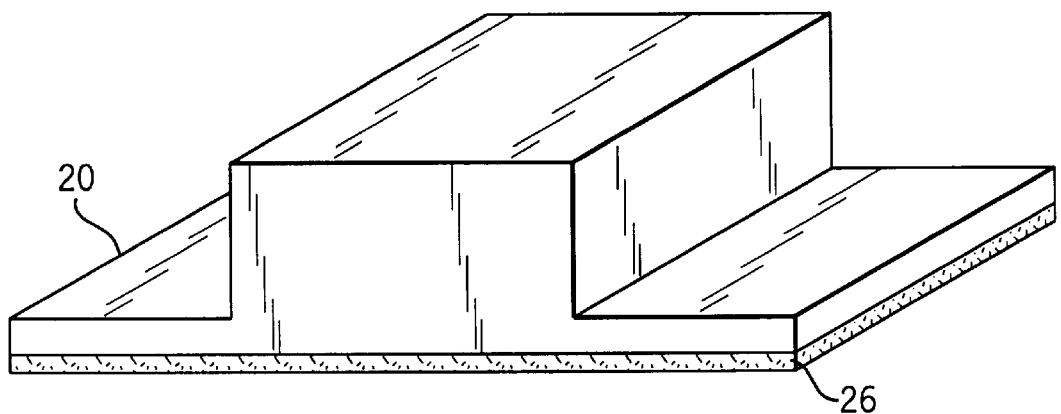
FIG. 4A is an electromagnetic position sensor including an adhesive cutaneous gel mount.
Figure 4B:
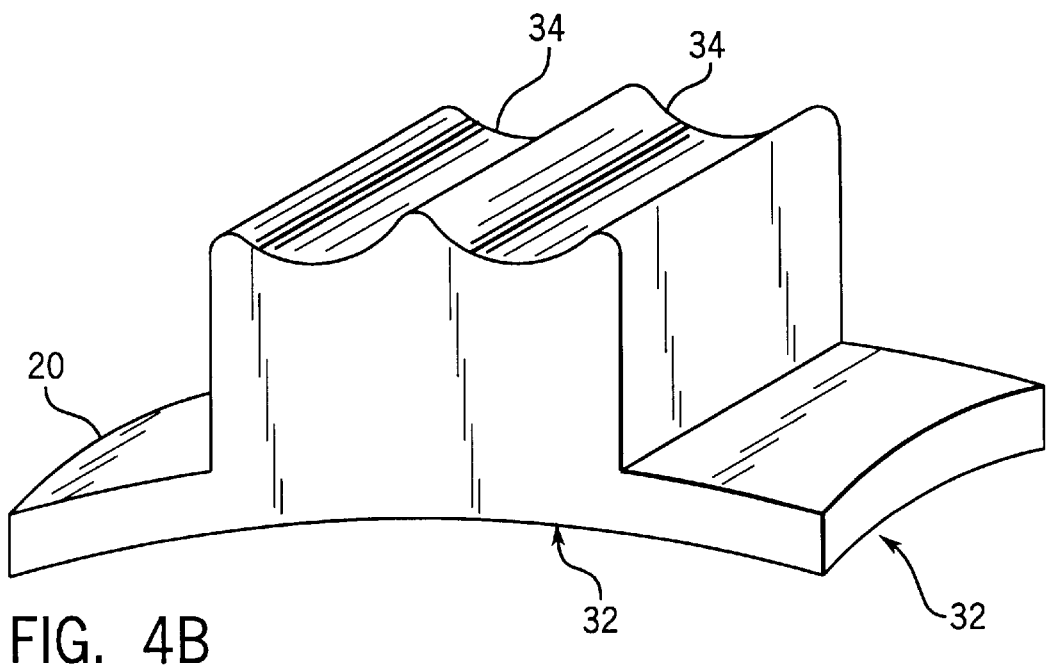
FIG. 4B is a view of an electromagnetic position sensor having a lower surface shaped to correspond to the front of a patient's shoulder and a top surface having a grip for the fingers of the examining physician.

The first position sensor 20A is preferably placed to the anterior of the patient's shoulder and held in place by a first hand 28A of the examining physician. The purpose of the first sensor 20A is to monitor the position of the humeral head 30. Preferably, the first position sensor 20A is held in place by the examining physician over the bicipital groove to the anterior of the shoulder joint. Normally, it will not be necessary, or even desirable, for adhesives such as tape or a cutaneous gel-based mount to be used on the first sensor 20A because the sensor 20A is held in place by the examining physician. However, as shown in FIG. 4B, it is desirable that the first sensor 20A have a bottom surface 32 that is shaped to conform to the shoulder of the patient, and thus facilitate stability and repeatability in the positioning of the sensor 20A with respect to the humeral head 30 of the patient. It is also desirable that the sensor 20A include finger grips 34 for the examiner's fingers. While it is preferred that the first sensor 20A be placed to the anterior of the shoulder joint in order to monitor the position of the humeral head, the first sensor 20A can also be placed to the posterior of the shoulder joint if it is located properly to monitor the position of the humeral head 30 during the examination. In any event, it is important that the second sensor 20B be placed in a position on the skin of the patient that accurately monitors the relative position of the glenoid of the scapula and that the first position sensor 20A be placed in a location that accurately monitors the position of the humeral head.

Figure 2:
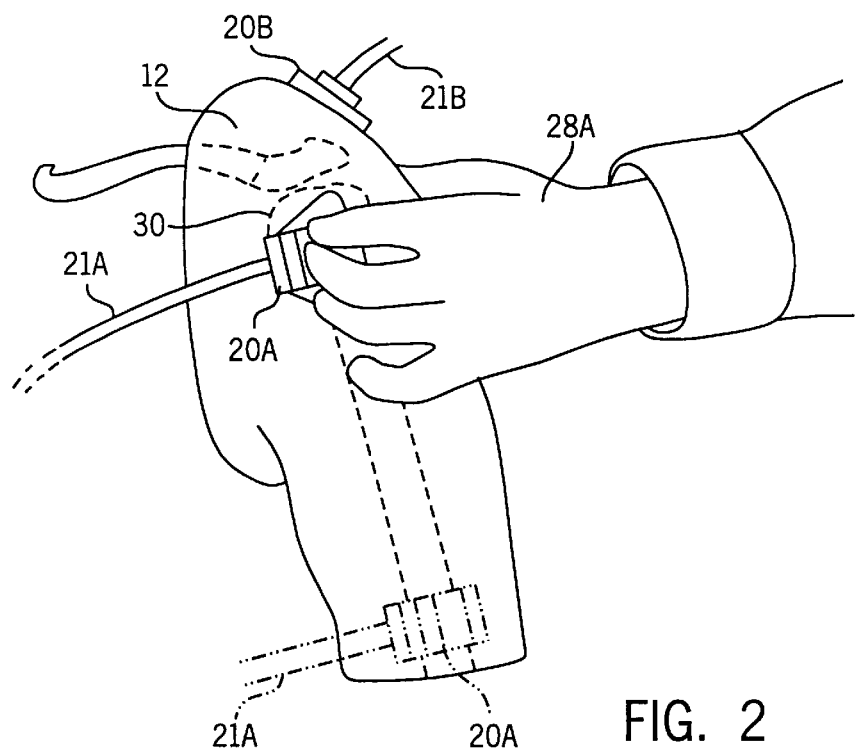
FIG. 2 is a detailed view showing the application of electromagnetic position sensors on the skin of a patient in accordance with monitoring shoulder joint translation during a glenohumeral examination, and in phantom for a shoulder joint range of motion examination.
Figure 3:
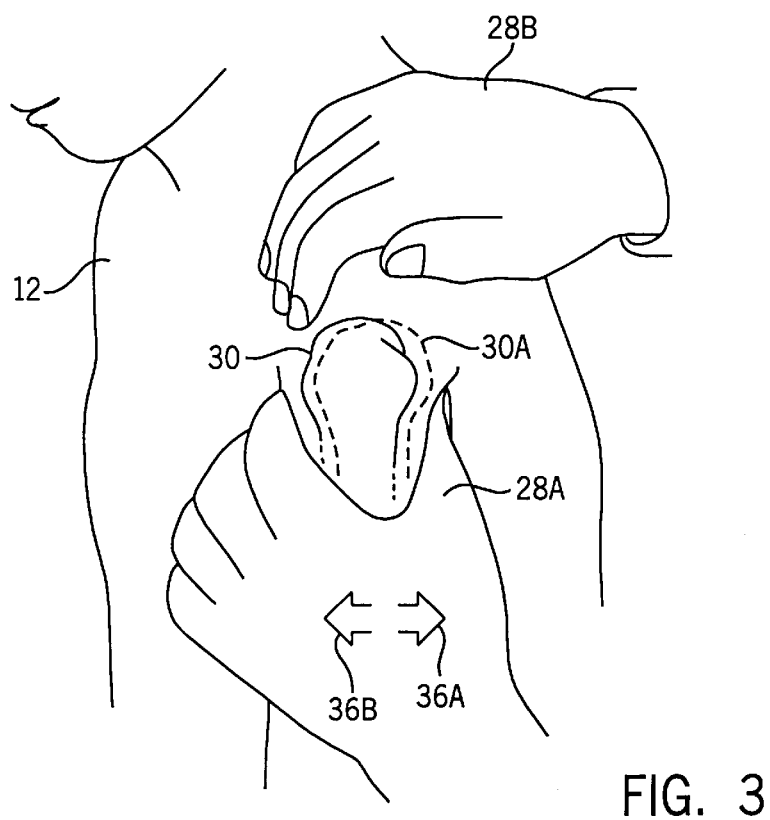
FIG. 3 is a schematic view illustrating a typical glenohumeral joint translation examination.

FIG. 3 shows an examining physician conducting a glenohumeral joint translation examination on the patient 12. The position sensors 20A and 20B are not shown in FIG. 3 for purposes of illustration, although the sensors 20A and 20B are preferably placed as shown in FIG. 2 to monitor the procedure in accordance with the invention. In FIG. 3, the patient 12 is in an upright position. One hand 28B of the examining physician grips the patient's shoulder from the rear of the patient as is conventional in the art (i.e., the physician preferably grips the scapular spine and the clavicle). The other hand 28A of the examining physician grips the patient's upper arm near the humeral head 30 as is also conventional in the art. The examining physician centers the humeral head 30 within the glenoid. The examining physician then applies a unidirectional force in a clinical direction, e.g. in the horizontal direction as depicted by arrows 36A and 36B in FIG. 3.

To monitor translation of the humeral head rearward, the examining physician applies force in the direction of arrow 36A to move the humeral head 30A rearward as shown in phantom to a clinical end point. The sensors 20A and 20B measure the difference in relative position between the humeral head 30 and the glenoid of the scapula as the humeral had 30 is moved from the centered position 30 to the clinical end point 30A. The procedure is also normally conducted to monitor forward translation of the humeral head 30 with respect to the glenoid of the scapula by applying a force in the direction of arrow 36B. As an alternative to the technique shown in FIG. 3, the patient 12 can be put into a supine position in which the patient 12 is lying on their back. Using the supine technique, the attending physician grasps the humeral head 30 of the patient 12 to move the humeral head 30 within the glenoid as the patient 12 remains in the supine position.

Although normal translation varies among individuals, a typical amount of translation for an individual with a healthy shoulder is about 8 millimeters, whereas translation in a shoulder injured due to incomplete or partial dislocation is typically in the range of 15 millimeters prior to surgery. The invention as described herein has been shown to be accurate within 1 millimeter, and results are highly reproducible. The accuracy of the cutaneous-mounted sensors has been tested on cadavers by comparing translation measurements using sensors mounted on rigid pins inserted into the bone as is known in the prior art to translation measurements using the cutaneously-mounted sensors as described herein. The interclass correlation coefficient (ICC) as used by Fleiss was used to determine the degree of agreement between absolute translation values made using the sensors mounted on rigid pins versus cutaneously-mounted sensors for both anterior and posterior translation examinations. ICC values greater than or equal to 0.80 show a high degree of agreement or good correlation between the measurements. The ICC for posterior translation during the testing was 0.86 and the ICC for anterior translation during the testing was 0.81. In addition, testing showed that the repeatability of measurements using cutaneous-mounted sensors for a glenohumeral examination in accordance with the invention is within 2%.

Figure 5:
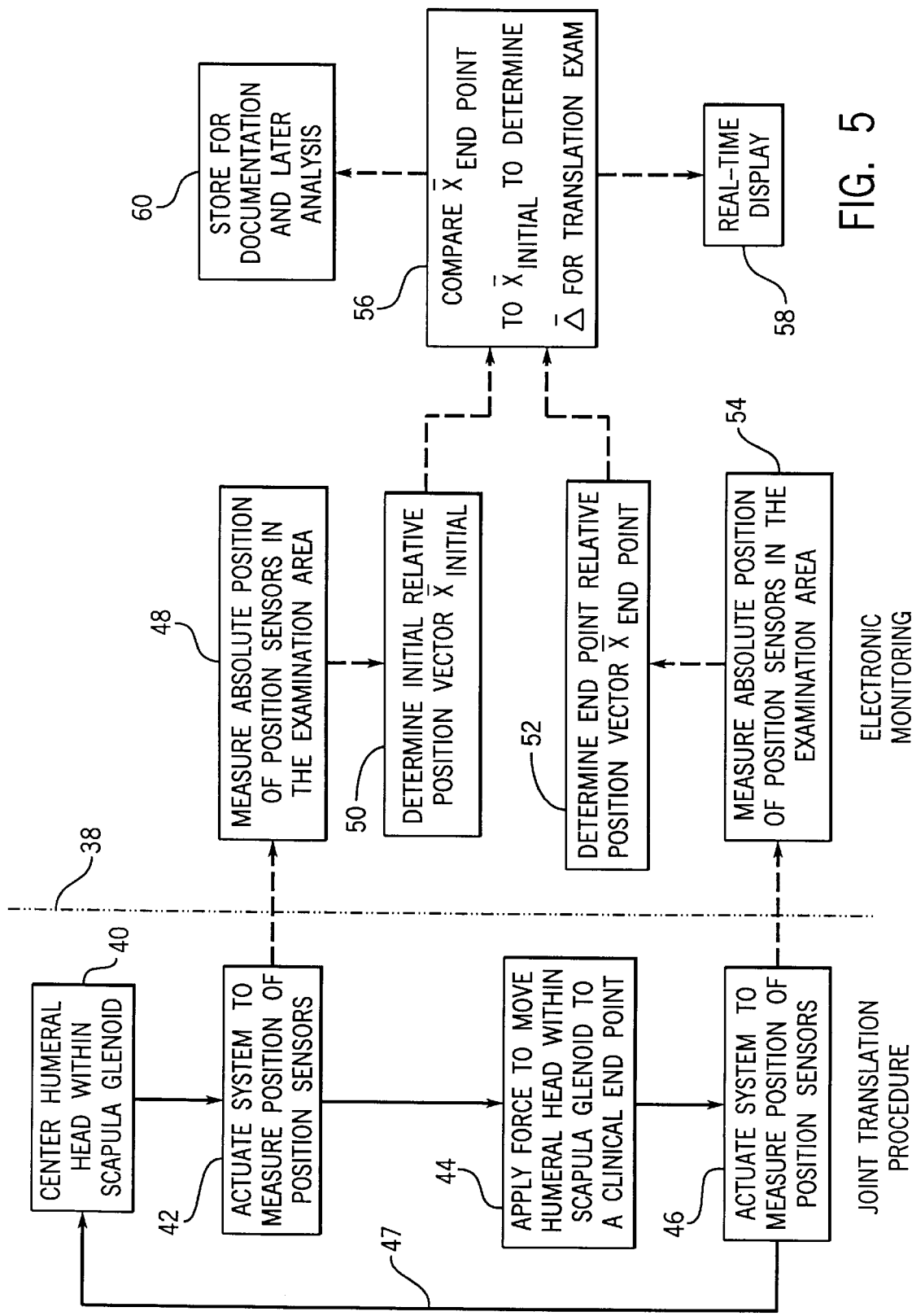
FIG. 5 is a flowchart illustrating the operation of the invention in conjunction with a joint translation examination procedure.

FIG. 5 is a block diagram illustrating the operational steps for implementing the invention to electronically monitoring joint translation during a glenohumeral examination after the sensors 20A, 20B have been properly positioned on the patient 12. In FIG. 5, blocks 40, 42, 44 and 46, which are located to the left of dashed/dotted line 38, represent procedural steps carried out by the examining physician and their assistant when conducting the translation examination procedure. Blocks 48, 50, 52, 54, 56, 58 and 60, which are located to the right of the dashed/dotted line 38, represent electronic monitoring and data analysis in accordance with the invention. Referring to the upper left corner of FIG. 5, block 40 illustrates that the translation examination procedure begins with the examining physician centering the humeral head within the glenoid of the scapula (as shown in FIG. 3). With the humeral head centered within the glenoid of the scapula, the physician's assistant actuates the system to take a measurement reading of the position of the position sensors 20A, 20B (see, block 42). In the preferred embodiment of the invention, the system is actuated by pressing a button on mouse 23 for the computer 22, FIG. 1. However, actuation can be accomplished in other ways such as pressing a selected button on the keypad for the computer 22. Block 48 illustrates that actuation (block 42) causes the system to record the absolute position $A_1$, $B_1$. of the position sensors 20A, 20B in the examination area 16. Block 50 illustrates that an initial relative position vector $\overline{X}_{initial}$ is determined from the absolute position $A_1$, $B_1$ of the sensors 20A and 20B respectively. The initial relative position vector $\overline{X}_{initial}$ is stored in memory on the computer 22.

Block 44 in FIG. 5 illustrates that the examining physician applies force in either the posterior clinical direction 36A, FIG. 3, or the anterior clinical direction 36B, FIG. 3, to a clinical end point. With the humeral head positioned at the clinical end point with respect to the glenoid of the scapula, the physician's assistant actuates the system to measure the position of the sensors 20A, 20B (see, block 46). Block 54 indicates that actuation causes the system to record the absolute position $A_2$, $B_2$ of the position sensors 20A, 20B when the humeral head is positioned at the clinical end point. A clinical end point relative position vector $\overline{X}_{end\ point}$ is determined as indicated by block 52 from the absolute positions $A_2$, $B_2$ of the position sensors 20A, 20B.

Block 56 illustrates that the clinical end point relative position vector $\overline{X}_{end\ point}$ is compared to the initial relative position vector $\overline{X}_{initial}$ to determine the translation $\overline{\Delta}$ for the examination. In general, translation $\overline{\Delta}$ is a vector quantity having both directional and magnitude information. However, the scalar value $\Delta$ representing the magnitude of translation may be sufficient in practice. The magnitude of translation $\Delta$ is preferably displayed in real time, block 58, on the screen display 24 of the computer 22. In addition, the translation information can be stored for documentation and later analysis, block 60.

Line 47 indicates in FIG. 5 that it is generally desirable to repeat each anterior and/or posterior translation examination. Normally, the examination should be repeated at least three times. Depending on the needs for the particular application, the information stored for documentation and/or later analysis, block 60, may include information for each specific measurement, or may merely contain average values for the examination.

Figure 6:
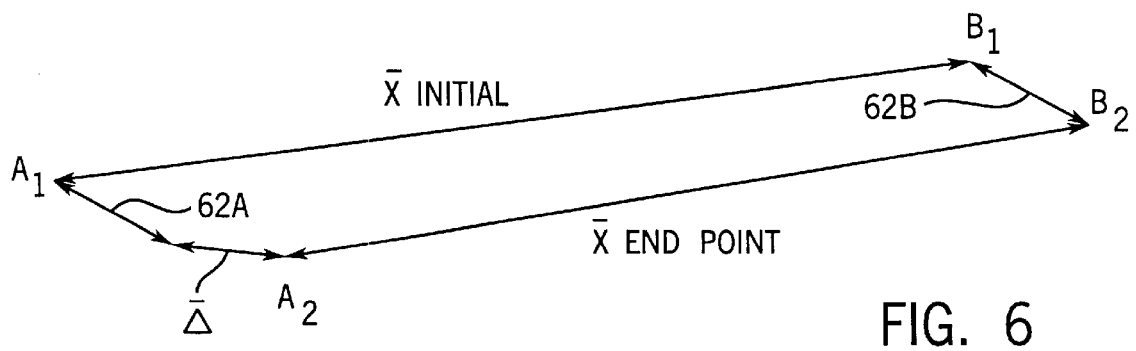
FIG. 6 is a vector diagram illustrating the measurement of joint translation in accordance with the invention.

FIG. 6 is a vector diagram illustrating the measurement of joint translation in accordance with the invention. In FIG. 6, the initial relative position vector $\overline{X}_{initial}$ is the relative distance between the absolute position of the position sensor 20A and the absolute position $B_1$ of the sensor 20B when the initial readings (blocks 42, 48 in FIG. 5) are taken. The clinical end point relative position $\overline{X}_{end\ point}$ is the difference between the absolute position $A_2$ of the first position sensor 20A when the humeral head is located at the clinical end point and the absolute position $B_2$ of the second sensor 20B when the humeral head is at the clinical end point. In general, the measured absolute position of both sensors 20A and 20B changes during the examination from the initial position to the clinical end point position. The translation $\overline{\Delta}$ is the difference between the relative positions of the sensors 20A, 20B. This is shown in FIG. 6 by illustrating that the translation $\overline{\Delta}$ vector is the difference between the measured absolute positions $A_1$, and $A_2$ of the first position sensor 20A shifted to account for vector 62A. Vector 62A has the same magnitude and direction of vector 62B which defines the difference in measured absolute position $B_1$, and $B_2$ of the second position sensor 20B.

Figure 7:
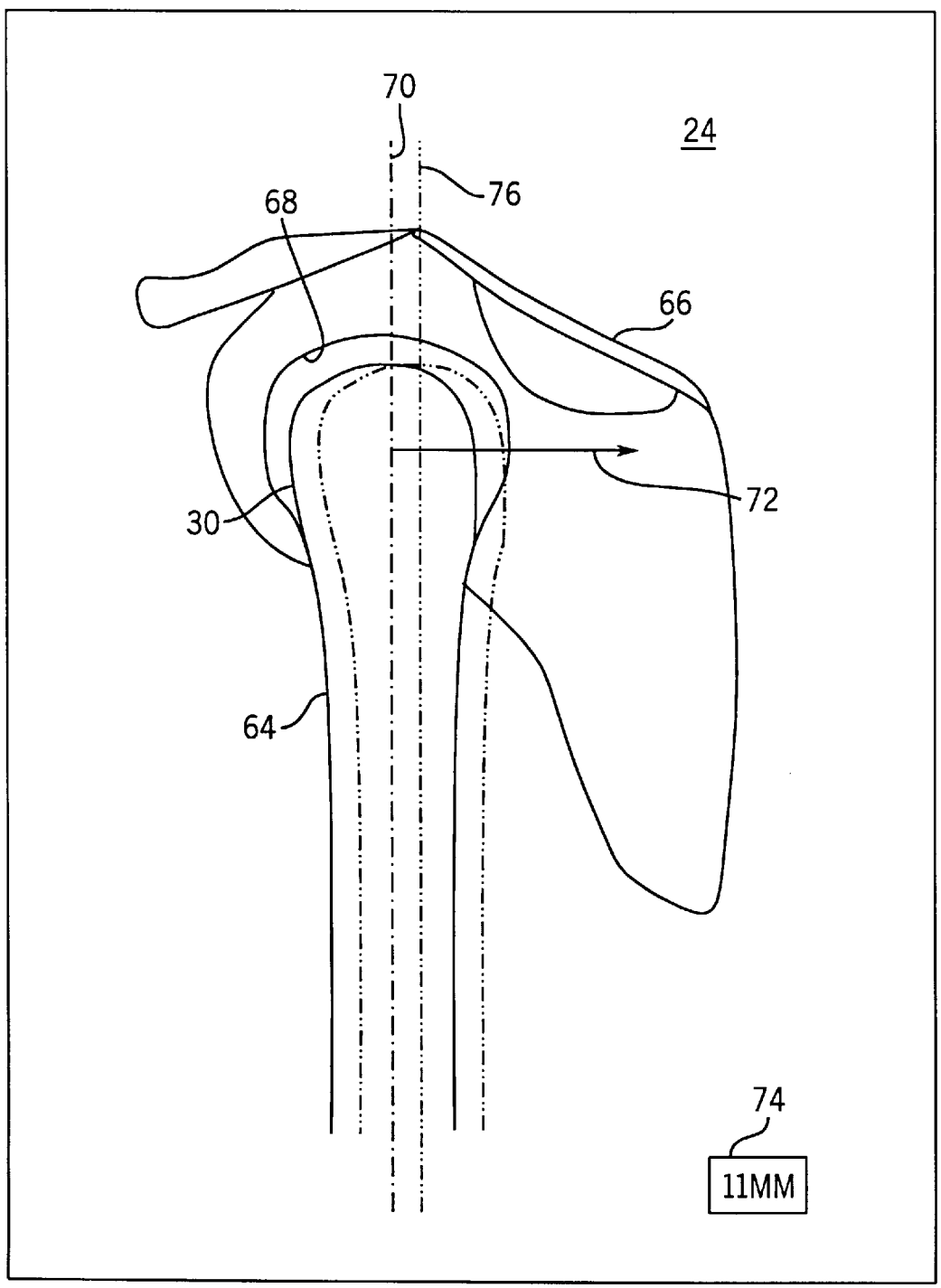
FIG. 7 is a schematic drawing of a screen display illustrating the amount of joint translation monitored by the invention during a glenohumeral examination.
Figure 8:
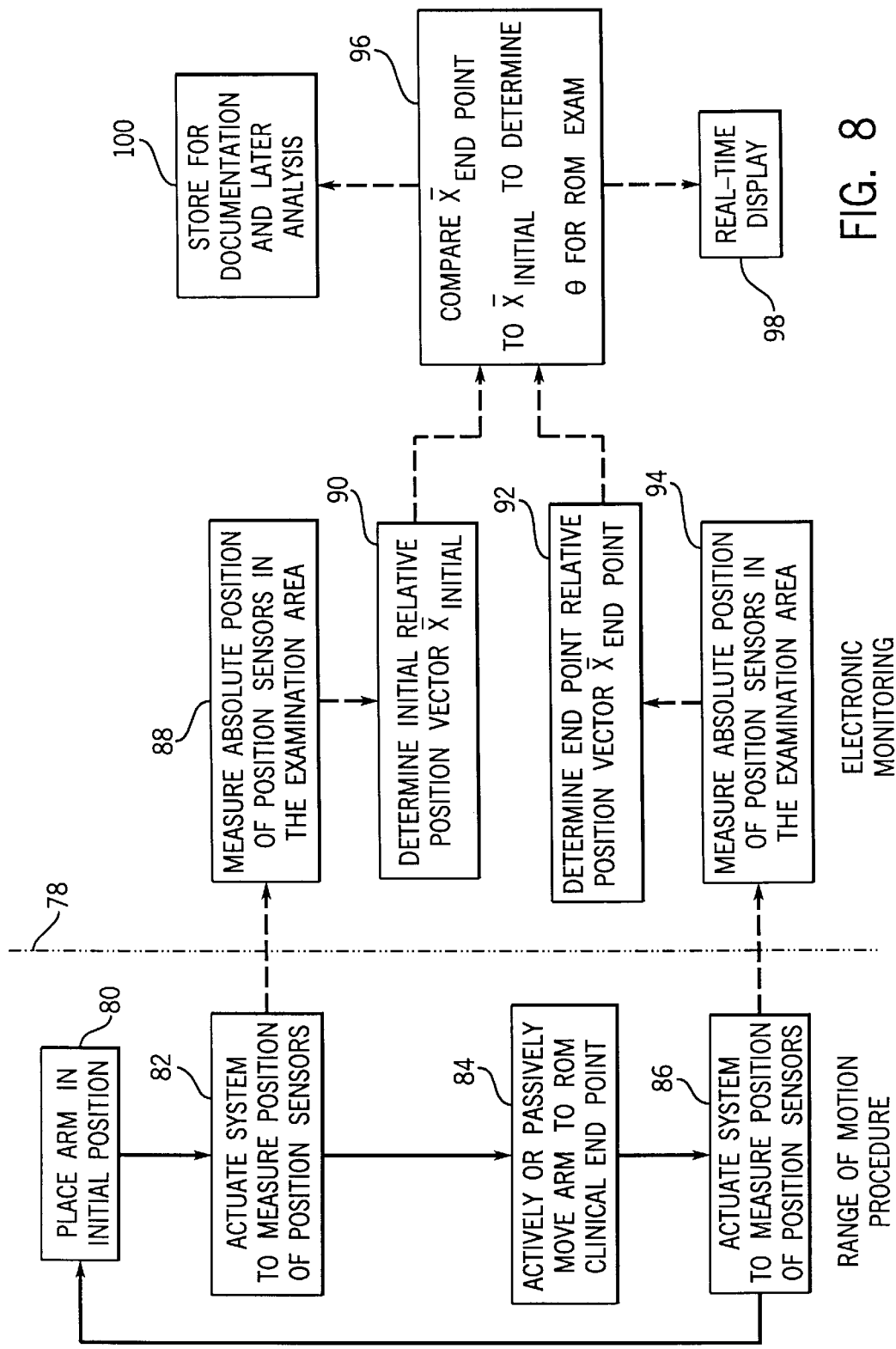
FIG. 8 is a flowchart illustrating the operation of the invention during a joint range of motion examination procedure.

Referring to FIG. 7, the screen display 24 preferably includes an image 64 of the humerus 30 in the vicinity of the glenohumeral joint and an image 66 of the scapula. The display 24 shows the humeral head 30 located within the glenoid 68 of the scapula 66. The display 24 thus provides a simulation of the glenohumeral joint on the screen display 24 during the translation examination. The image 64 of the humerus moves on the screen display 24 in proportion to the translation vector $\overline{\Delta}$ (i.e. the relative movement of the first position sensor 20A with respect to the second position sensor 20B). Reference grid line 70 appears on the screen display 24, and corresponds to the initial position of the humeral head 30 within the glenoid 68 of the scapula as measured by the system. When the physician provides force to move the humeral head 30 to the clinical end point and the system is actuated to take measurement, the image 64 of the humerus shifts on the screen display 24 as shown in phantom in FIG. 7. In addition, arrow 72 appears on the screen display 24 to indicate the general direction of translation. The magnitude of translation is displayed on the screen 24 numerically within box 74 in the lower right corner of the screen 24. While reference grid line 70 remains fixed, grid line 76 is displaced in proportion with the image 64 of the humerus at the measured clinical end point. In this manner, the amount of translation can be observed quickly upon viewing the screen display 24 and judging the distance between grid lines 70 and 76.

In the embodiment of the screen display 24 shown in FIG. 7, the image 66 of the scapula remains fixed on the screen, and displacement of the image 64 of the humerus represents the relative displacement between sensors 20B and 20A. However, in certain applications it may be desirable that both images 64 and 60 displace on the screen display 24 in accordance with the absolute position of the respective sensors 20B, 20A. Also, it may be desirable to provide additional information on the screen display 24. For instance, it may be desirable to display the clinical direction of translation in terms of angle attitude, as well as provide historical information relating to the patient and/or the examination. It may also be desirable to store this type of information for documentation and/or later analysis (see block 60 in FIG. 5).

As mentioned above, it may be desirable to use the invention to monitor joints other than the shoulder joint. Therefore, it may be desirable for the computer 22 to store various sets of images to simulate various joints such as the knee, ankle, etc.

The invention can also be used to monitor joint range of motion procedures in much the same manner. Referring again to FIG. 1, the second position sensor 20B is adhered to the skin over the scapular spine or preferably over the acromion for a shoulder range of motion examination. When conducting a range of motion examination, it is normally important (depending on the sophistication of the software) to ensure that the sensor 20B is placed to accurately measure the position of the shoulder joint. On the other hand, the first position sensor 20A is preferably located on the skin over the patient's biceps, which is shown in phantom in FIG. 1. When implementing a shoulder examination, the first sensor 20A should be adhered to the arm using tape or a cutaneous gel mount as described with respect to FIG. 4A. To conduct a shoulder range of motion examination, the patient 12 holds their arm straight downward by their side and rotates their arm so that the palm of their hand is facing forward. The patient 12 is then instructed to raise their arm in a circular fashion keeping the arm straight and the palm pointed forward (i.e. abduction). Active range of motion is observed by instructing the patient to raise the arm to its limit (i.e. an active ROM clinical end point). Passive range of motion is observed by applying force to the arm to move the arm to a passive ROM clinical end point (i.e. passive ROM clinical end point) which lies beyond the active ROM clinical end point. With the position sensors 20A, 20B in place, the invention can be used to objectively monitor these types of shoulder range of motion examinations.

FIG. 8 is a block diagram showing the implementation of the invention to monitor a shoulder range of motion examination once the sensors 20A, 20B are properly placed on the patient 12. In the upper left of FIG. 8, block 80 indicates that the patient places their arm in the initial position for the range of motion procedure. The system is then actuated, as indicated by block 82, to measure the absolute position of the sensors 20A, 20B. Again, actuation is preferably accomplished by pressing a button on the mouse 23 for the computer 22. Block 88 indicates that actuation of the mouse 23 causes the system to record the absolute position $A_1$, $B_1$ of the sensors 20A, 20B, respectively. The initial relative position vector $\overline{X}_{initial}$ is then determined from the absolute initial positions $A_1$, $B_1$, as illustrated by block 90. In an active range of motion exam, the patient is then instructed to raise their arm to the clinical end point, block 84. Block 86 indicates that the system is then actuated to measure the absolute position $A_2$, $B_2$ of the sensors 20A, 20B with the arm in the clinical end point. Actuation causes the system to record the absolute positions $A_2$, $B_2$ of the sensors 20A, 20B (block 94) and the end point relative position vector $\overline{X}_{active}$ for the active exam is calculated (block 92). The range of motion $\theta_{active}$ for the active range of motion exam is calculated by comparing $\overline{X}_{active}$ to $\overline{X}_{initial}$ and accounting for the movement of the second position sensor 20B (i.e. the difference between measured absolute positions $B_1$ and $B_2$). FIG. 9 is a vector diagram illustrating these relationships. Block 98 in FIG. 8 illustrates that this information can be shown on a real time display, preferably in a manner similar to that shown in FIG. 7, except modified to accommodate a range of motion examination. Line 87 in FIG. 8 indicates that the test is normally repeated as with the translation examinations. Block 100 indicates that measured information, either specific or averaged, can be stored for documentation and/or later analysis in the computer 22. For a passive range of motion examination, the procedure is similar to the above described procedure for an active range of motion exam, except force is applied to move the arm to a passive clinical end point normally located over the patient's shoulder, block 84. When the passive clinical end point is reached, the system is again actuated (block 86) to measure the absolute position $A_3$, $B_3$ of the position sensors 20A, 20B (block 94). From the absolute position values $A_3$, $B_3$ at the passive clinical end point, the passive clinical end point relative position vector $\overline{X}_{passive}$ is determined. The range of motion for the passive examination $\Theta_{passive}$ is determined by comparing $\overline{X}_{initial}$ to $\overline{X}_{passive}$ in a manner similar to that described above for the active range of motion examination.

In a shoulder range of motion examination as described herein, it is desirable to maintain the motion of the arm within a single plane. In some cases, it may be desirable to measure range of motion in more than one plane. The invention contemplates modifying the system to accommodate additional dimensions, such as Z-axis motion or rotational displacement. The invention also contemplates the use of the system to monitor and display range of motion examinations of other joints or parts of the human body, including for instance the knee joint, the ankle joint, the elbow, and the neck.

Those skilled in the art should appreciate that the invention provides non-invasive means to accurately and objectively monitor joint laxity and range of motion in a convenient, cost-effective manner, without subjecting patients to radiation. The objective data is easily displayed and stored for documentation or later analysis. It should also be noted that the invention has been described herein with respect to exemplary embodiments, but it is recognized that various modifications, alternatives, and equivalents may be apparent to those skilled in the art. For instance, as mentioned, the invention can be used to objectively monitor translation and/or range of motion of joints or groups of joints other than the shoulder joint. The following claims should be interpreted to cover such modifications, alternatives or equivalents.

We claim:

1. In a patient having a first bone and a second bone which are articulated at a joint, a non-invasive method of objectively measuring joint translation at the joint in a clinical setting comprising the steps of
    a) placing a first position sensor on the surface of the skin of a patient to measure the position of the first bone in the vicinity of the joint;
    b) generating a first position signal in response to the position of the first position sensor;
    c) placing a second position sensor on the surface of the skin of the patient to measure the position of the second bone in the vicinity of the joint;
    d) generating a second position signal in response to the position of the second position sensor;
    e) positioning the first bone and the second bone with respect to each other in a clinical neutral position at the joint and storing the value of the first and second position signals when the first and second bones are positioned in the clinical neutral position;
    f) using the stored value of the first and second position signals when the first and second bones are positioned in the clinical neutral position to determine the relative position between the first and second electromagnetic position sensors when the first and second bones are positioned in the clinical neutral position;
    g) applying force to move the first bone in the vicinity of the joint with respect to the second bone in the vicinity of the joint to a clinical end point and storing the value of the first and second position signals when the first and second bones are positioned at the clinical end point;
    h) using the stored values of the first and second position signals when the first and second bones are positioned at the clinical end point to determine the relative position between the first and second position sensors when the first bone in the vicinity of the joint is positioned at the clinical end point with respect to the second bone in the vicinity of the joint; and
    i) determining the translation of the joint by comparing the relative position between the first and second position sensors when the first and second bones are in the clinical neutral position to the relative position between the first and second position sensors when the first bone is positioned at the clinical end point with respect to the second bone.

2. A method of objectively measuring joint translation as recited in claim 1 wherein steps e) through i) are repeated at least three times during an examination.

3. A method of objectively measuring joint translation as recited in claim 1 wherein the first and second position sensors are electromagnetic position sensors and the method further comprises the step of providing a low-level electromagnetic field within a patient examination area and further wherein the first position signal is generated in response to the position of the first electromagnetic position sensor within the low-level electromagnetic field and the second position signal is generated in response to the position of the second electromagnetic position sensor within the low-level electromagnetic field.

4. A non-invasive system for objectively measuring joint translation in a joint of a patient comprising:
    an electromagnetic transmitter that produces a magnetic field in an examination area;
    a first electromagnetic position sensor that generates a first position signal in response to the position of the first electromagnetic position sensor in the magnetic field, where the first electromagnetic position sensor is configured for placement on the surface of the skin of the patient over a first bone in the vicinity of the joint;

a second electromagnetic position sensor that generates a second position signal in response to the position of the second electromagnetic position sensor in the magnetic field, wherein the second electromagnetic position sensor is part of a sensor assembly that includes means for mounting the second sensor on the surface of the skin of the patient over a second bone in the vicinity of the joint; and a programmed computer that receives the first and second position signals, the programmed computer including means for objectively determining joint translation of the joint when the patient undergoes a joint translation examination with the first electromagnetic position signal placed on the surface of the skin of the patient over the first bone in the vicinity of the joint and the second electromagnetic position sensor placed on the surface of the skin of the patient over the second bone in the vicinity of the joint.

5. A system as recited in claim 4 further comprising a screen display which includes an image of the first bone at least in the vicinity of the joint and an image of the second bone at least in the vicinity of the joint, wherein the image of the first bone moves relative to the image of the second bone in proportion to the movement of the first electromagnetic position sensor with respect to the second electromagnetic position sensor.

6. A system as recited in claim 4 wherein the first electromagnetic position sensor is part of a sensor assembly that includes a cutaneous mount for the sensor assembly.

7. A system as recited in claim 4 wherein the second electromagnetic position sensor is part of a sensor assembly that includes a contoured outer surface that facilitates the gripping of the sensor assembly in the fingers of a physician performing the joint translation examination.

8. A non-invasive method of objectively measuring glenohumeral translation in a patient in a clinical setting comprising the steps of:

a) placing a scapula position sensor on the surface of the skin of a patient over the patient's scapula;

b) generating a scapula position signal in response to the position of the scapular position sensor;

c) placing a humeral head position sensor on the surface of the skin of the patient at a location corresponding to the humeral head of the patient;

d) generating a humeral head position signal in response to the position of the humeral head position sensor;

e) centering the humeral head within a glenoid of the scapula, and storing the values of the scapula position signal and the humeral head position signal when the humeral head is centered within the glenoid of the scapula;

f) using the stored values of the scapula position signal and the humeral head position signal to determine the relative position between the scapula position sensor and the humeral head position sensor when the humeral head is centered within the glenoid of the scapula;

g) applying force to move the humeral head with respect to the glenoid of the scapula to a clinical end point, and storing the values of the scapula position signal and the humeral head position signal when the humeral head is positioned at the clinical end point with respect to the glenoid of the scapula;

h) using the stored values of the scapula position signal and the humeral head position signal to determine the relative position between the scapula position sensor and the humeral head position sensor when the humeral head of the patient is positioned at the clinical end point with respect to the glenoid of the scapula;

i) determining glenohumeral translation by comparing the relative distance between the scapula position sensor and the humeral head position sensor when the humeral head is centered in the glenoid to the relative distance between the scapular position sensor and the humeral head position sensor when the humeral head is positioned at the clinical end point with respect to the glenoid.

9. A method of objectively measuring glenohumeral translation as recited in claim 8 wherein the scapular position sensor and the humeral head position sensors are electromagnetic position sensors and the method further comprises the step of providing a low-level electromagnetic field within a patient examination area and further wherein the scapula position signal is generated in response to the position of the scapular position sensor within the low-level electromagnetic field and the humeral head position signal is generated in response to the position of the humeral head position sensor within the low-level electromagnetic field.

10. A method of objectively measuring glenohumeral translation as recited in claim 8 wherein steps e) through i) are repeated at least three times.

11. A method as recited in claim 8 wherein the humeral head position sensor is placed on the surface of the skin of the patient over an anterior portion of the humeral head.

12. A method as recited in claim 8 wherein the humeral head position sensor is placed on the surface of the skin of the patient over a posterior portion of the humeral head of the patient.

13. A method as recited in claim 8 wherein the humeral head position sensor is placed on the surface of the skin of the patient over the bicipital groove at the anterior of the patient's shoulder.

14. A method as recited in claim 8 wherein the scapula position sensor is placed on the surface of the skin over the acromion portion of the scapula.

15. A method as recited in claim 8 wherein the scapula position sensor is placed on the surface of the skin over the spine of the scapula.

16. A method as recited in claim 8 wherein the scapula position sensor is temporarily adhered directly on to the surface of the skin of the patient when the scapular position sensor is placed on the skin over the patient's scapula using a cutaneous mount.

17. A method as recited in claim 8 wherein the humeral head position sensor is held in a hand of a person applying force to move the humeral head with respect to the scapula.

18. A method as recited in claim 8 further comprising the step of:

placing the patient in an upright position;

wherein force is applied to move the humeral head of the patient with respect to the scapula of the patient by grasping the scapular spine and the clavicle of the patient with a first hand, grasping the humeral head of the patient with a second hand, and moving the humeral head within the glenoid of the scapula either anteriorly or posteriorly to a clinical end point.

19. A method as recited in claim 8 further comprising the step of:

lying the patient in a supine position; wherein force is applied to move the humeral head of the patient with respect to the glenoidal of the patient by grasping the humeral head of the patient and moving the humeral head relative to the glenoid to a clinical end point as the patient remains in the supine position.

20. A method as recited in claim 8 further comprising the steps of:

selecting a clinical linear direction of measuring glenohumeral translation;

defining an initial relative position vector from the stored values of the scapula position signal and the humeral head position signal when the humeral head is centered within the glenoid of the scapula;

defining an end point relative position signal from the stored values of the scapula position signal and the humeral head position signal when the humeral head is positioned at the clinical end point with respect to the glenoid of the scapula;

determining a translation vector from the initial relative position vector and the end point relative position vector;

determining whether force applied to move the humeral head with respect to the glenoid is applied in the clinical linear direction by comparing the direction of the translation vector to the clinical linear direction.

21. In a patient having a first bone and a second bone articulated at a joint, a non-invasive method of objectively measuring range of motion of the joint in a clinical setting comprising the steps of:

a) placing a first position sensor on the surface of the skin of the patient to measure the position of the first bone in the vicinity of the joint;

b) generating a first position signal in response to the position of the first position sensor;

c) placing a second position sensor on the surface of the skin of the patient to measure the position of the second bone;

d) generating a second position signal in response to the position of the second position sensor;

e) placing the second bone at an initial position and storing the value of the first and second position signals when the second bone is in the initial position;

f) actively or passively moving the second bone through a clinical range of motion examination to a clinical end point and storing the value of the first and second position signals when the second bone is positioned at the clinical end point; and g) objectively determining the range of motion of the joint by comparing the relative position of the first and second position sensors when the second bone of the patient is in the initial position to the relative position of the first and second sensors when the second bone of the patient is positioned at the range of motion clinical end point.

22. A method of objectively measuring range of motion as recited in claim 21 wherein the second position sensor is placed on the surface of the skin of the patient over the second bone of the patient at a location away from the joint.

23. A method of objectively measuring range of motion as recited in claim 21 wherein the first and second position sensors are electromagnetic position sensors and the method further comprises the step of providing a low-level electromagnetic field within a patient examination area; and further wherein the first position signal is generated in response to the position of the first electromagnetic position sensor in the electromagnetic field and the second position signal is generated in response to the position of the second electromagnetic position sensor within the electromagnetic field.

24. A method of objectively measuring range of motion as recited in claim 21 wherein steps e) through g) are repeated at least three times.

25. A method of objectively measuring range of motion as recited in claim 21 further comprising the steps of:

selecting a clinical range of motion plane;

defining an initial relative position vector from the stored values of the first and second position signals when the second bone is in the initial position;

defining an end point relative position vector from the stored values of the first and second position signals when the second bone is positioned at the clinical end point;

determining a range of motion vector from the initial relative position vector and the end point relative position vector; and determining whether the second bone has been moved during the clinical range of motion examination within the selected clinical range of motion plane by comparing the direction of the range of motion vector to the clinical range of motion plane.

26. For use with a patient having a first bone and a second bone which are articulated at a joint, a non-invasive electromagnetic monitoring system for objectively measuring range of motion of the joint comprising:

an electromagnetic transmitter that produces a magnetic field in an examination area;

a first electromagnetic position sensor that generates a first position signal in response to the position of the first electromagnetic position sensor in the magnetic field, wherein the first electromagnetic position sensor is configured for placement on the surface of the skin of the patient over the second bone articulated at the joint;

a second electromagnetic position sensor that generates a second position signal in response to the position of the second electromagnetic position sensor in the magnetic field, wherein the second electromagnetic position sensor is configured for placement on the surface of the skin of the patient over the second bone articulated at the joint; and a programmed computer that receives the first and second position signals, the programmed computer including means for objectively determining joint range of motion when the patient undergoes a range of motion examination with the first electromagnetic position sensor placed on the surface of the skin of the patient over the first bone in the vicinity of the joint and the second electromagnetic position sensor placed on the surface of the skin of the patient over the second bone.

27. A system as recited in claim 26 further comprising a screen display including an image of the first bone at least in the vicinity of the joint and an image of the second bone at least in the vicinity of the joint, wherein the image of the first bone moves relative to the image of the second bone on the screen display in proportion to the movement of the first electromagnetic position sensor relative to the second electromagnetic position sensor.

28. A system as recited in claim 26 wherein the first electromagnetic position sensor is part of a first sensor assembly that includes a cutaneous mount for the first sensor assembly and the second electromagnetic position sensor is part of a second sensor assembly that includes a cutaneous mount for the second sensor assembly.

29. A method of objectively measuring joint translation as recited in claim 1 further comprising the steps of:

selecting a clinical linear direction of measuring joint translation;

defining an initial relative position vector from the stored values of the first position signal and the second position signal when the first and second bones are positioned in the clinical neutral position;

defining an end point relative position vector from the stored values of the first position signal and the second position signal when the first and second bones are positioned at the clinical end point;

determining a translation vector from the initial relative position vector and the end point relative position vector; and determining whether force applied to move the first bone with respect to the second bone in the vicinity of the joint is applied in the clinical linear direction by comparing the direction of the translation vector to the selected clinical linear direction.

* * * * *